(12) United States Patent
Mitchell

(10) Patent No.: US 10,993,854 B2
(45) Date of Patent: May 4, 2021

(54) DEVICE WITH AN IMPACTED CYLINDER CORE

(71) Applicant: Ponecha Mitchell, Middlesex, NC (US)

(72) Inventor: Ponecha Mitchell, Middlesex, NC (US)

( * ) Notice: Subject to any disclaimer, the term of this patent is extended or adjusted under 35 U.S.C. 154(b) by 300 days.

(21) Appl. No.: 15/730,269

(22) Filed: Oct. 11, 2017

(65) Prior Publication Data
US 2018/0214322 A1 Aug. 2, 2018

Related U.S. Application Data

(60) Provisional application No. 62/406,534, filed on Oct. 11, 2016.

(51) Int. Cl.
| | |
|---|---|
| *A61F 13/531* | (2006.01) |
| *A61F 13/47* | (2006.01) |
| *A61F 13/472* | (2006.01) |
| *A61F 13/53* | (2006.01) |

(52) U.S. Cl.
CPC ............ *A61F 13/531* (2013.01); *A61F 13/47* (2013.01); *A61F 13/47218* (2013.01); *A61F 13/47236* (2013.01); *A61F 2013/530029* (2013.01); *A61F 2013/530868* (2013.01)

(58) Field of Classification Search
CPC .............. A61F 13/531; A61F 13/47218; A61F 13/47236; A61F 2013/530029; A61F 2013/530868; A61F 13/47–476; A61F 2013/4706–472
See application file for complete search history.

(56) References Cited

U.S. PATENT DOCUMENTS

| | | | | |
|---|---|---|---|---|
| 5,947,945 A | * | 9/1999 | Cree .................... | A61F 13/4702 604/368 |
| 5,961,508 A | * | 10/1999 | Mayer ............... | A61F 13/47227 604/385.03 |
| 6,562,192 B1 | * | 5/2003 | Hamilton .......... | A61F 13/15634 162/141 |
| 6,617,490 B1 | * | 9/2003 | Chen ................. | A61F 13/15707 604/379 |
| 2004/0067214 A1 | * | 4/2004 | Krautkramer ..... | A61F 13/47218 424/76.3 |
| 2009/0204092 A1 | * | 8/2009 | Loyd ..................... | A61F 13/472 604/385.03 |
| 2010/0318056 A1 | * | 12/2010 | Tucker .............. | A61F 13/47227 604/387 |
| 2012/0157950 A1 | * | 6/2012 | Geilich ............... | A61F 13/5116 604/366 |
| 2014/0039440 A1 | * | 2/2014 | Doescher .............. | A61F 13/472 604/385.03 |
| 2014/0230831 A1 | * | 8/2014 | Zaltsberg .................. | A61F 5/30 128/891 |
| 2015/0272787 A1 | * | 10/2015 | Seitz ................. | A61F 13/47218 604/385.01 |

* cited by examiner

*Primary Examiner* — Adam Marcetich
*Assistant Examiner* — Meagan Ngo
(74) *Attorney, Agent, or Firm* — NCCU IP Clinic

(57) ABSTRACT

An adsorbent pad including an elongated core positioned substantially in the center of the pad, wherein the core protrudes out of the top surface of the pad. The adsorbent pad helps to direct the flow of fluids such as urine and blood to the elongated core, so that the wearer of the pad experiences less leakage of fluids to help with leaks better coverage throughout the use of the pad.

9 Claims, 12 Drawing Sheets

299

301

302

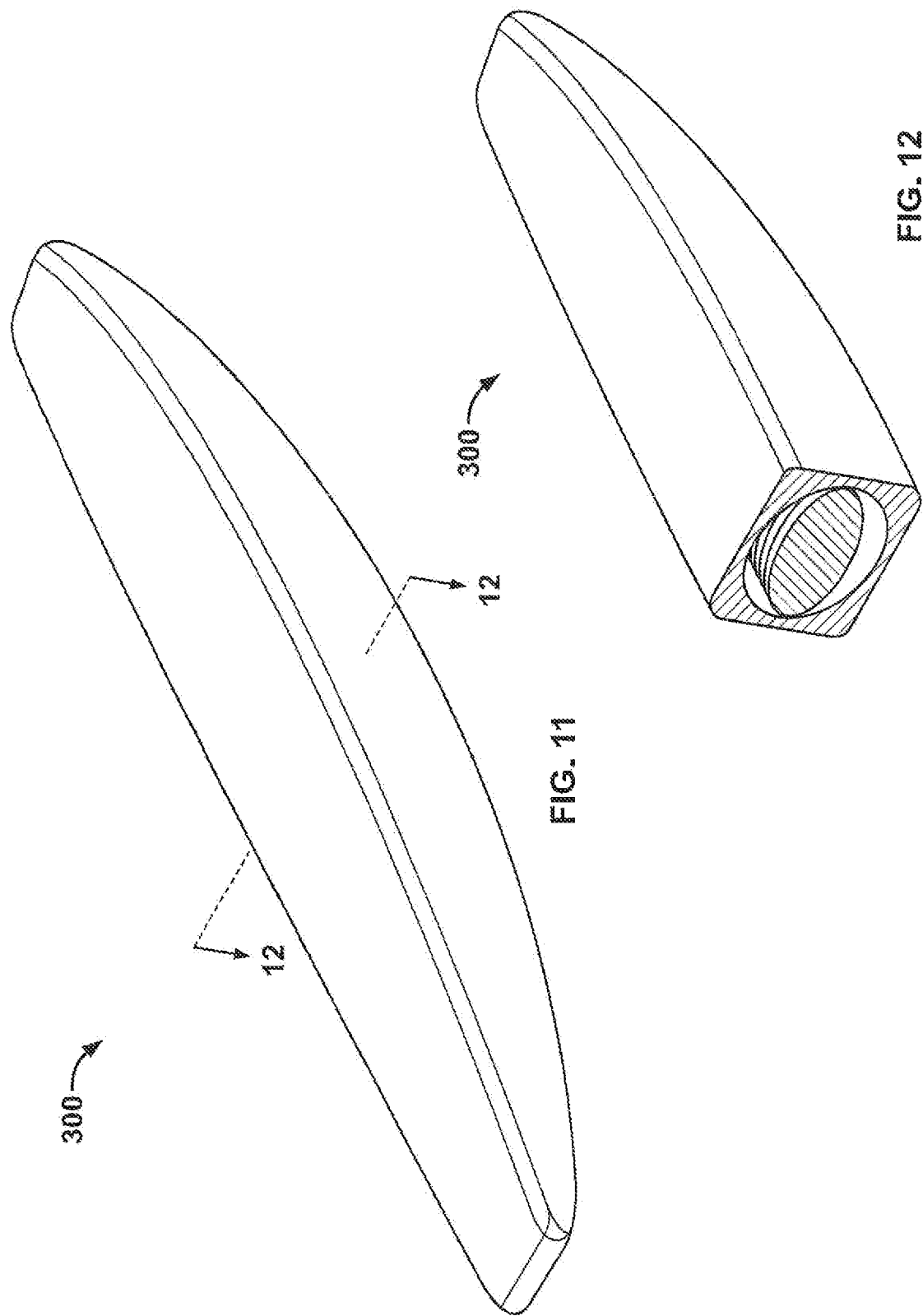

DEVICE WITH AN IMPACTED CYLINDER CORE

CROSS REFERENCE TO RELATED APPLICATIONS

This application claims priority to U.S. Provisional Application No. 62/406,534 filed Oct. 11, 2016. The content of the above application is incorporated by reference in its entirety.

FIELD OF THE INVENTION

The present application relates to a newly designed sanitary pad that includes an added core or cylinder that allows for better control of fluids.

BACKGROUND OF THE INVENTION

There is a strong need for an update to the sanitary pad and incontinence industries. Nearly every single female will experience issues with the existing design of their feminine pad(s). Also, a staggering number of men and women are experiencing health issues resulting in incontinence. Many of these products have fallen short, from leaking, not being the right size/fit, to not even being absorbent enough. Millions of women suffer from excessive bleeding during their menstrual cycles. This is due to a variety of reasons, such as fibroids, post hysterectomies and menorrhagia (if her cycle is excessively heavy, prolonged, or irregular). This can cause her to soak through a sanitary pad in an hour, for several hours at a time.

These are just a few of the impact these conditions and many more can have on a female's daily routine:
- Doubling-up on protection by needing both a sanitary pad and tampon
- Wake up during the night because she need to change clothes and bedding.
- A lot of clots during her flow.
- Periods lasting more than a week.
- Can't participate in your normal activities because your flow is too heavy.
- Have signs of anemia, which include fatigue, pale skin, shortness of breath and dizziness
- Inconvenience at work, home or play Although we can't control the amount or length of the menstrual cycle, we can direct the flow to the pad, where it belongs and not clothes or bedding.

The disclosed impacted cylinder core containing device also addresses incontinence issues that many men and women are experiencing. Currently, over 25 million people in North America alone, experience incontinence. While it is not a symptom of old age, rates of incontinence increase above age 65. With more people developing more and more health issues, such as strokes, infections, nerve damage from diabetes, incontinence is now becoming an epidemic. Incontinence can be caused by a variety of conditions and disorders (many times permanent problems), such as:
- Birth defects, pelvic injuries or surgeries, damage to the spinal cord, neurological diseases, multiple sclerosis (MS), infections, and changes that are a result of aging.
- Exercising, excessive laughter, coughing, or sneezing.
- Often women leak urine when they are pregnant or after they have given birth.
- Women who have stopped having their periods-menopause-often report bladder control problems.
- Athletes of all ages and genres sometimes have urine leakage during strenuous sports activities.
- Obesity

SUMMARY OF THE INVENTION

The new design includes a firm, round, elongated cylinder in the middle of the pad.

This helps direct the flow of the fluids to the center of the pad, and regardless of the rate of flow or length of use the fluids will continue down into the pad itself. The firm round elongated cylinder also helps to keep the sanitary pad in place against the individual and not just where ever the pad aligns with the individual's undergarments.

BRIEF DESCRIPTION OF THE DRAWINGS

In the following detailed portion of the present description, the teachings of the present application will be explained in more detail with reference to the example embodiments shown in the drawings, in which:

FIG. 11 is a top view of the one of the exemplary embodiments of cylindrical core of the device.

FIG. 12 is a cross section of the cylindrical core of the device.

DETAILED DESCRIPTION

Figure 1:
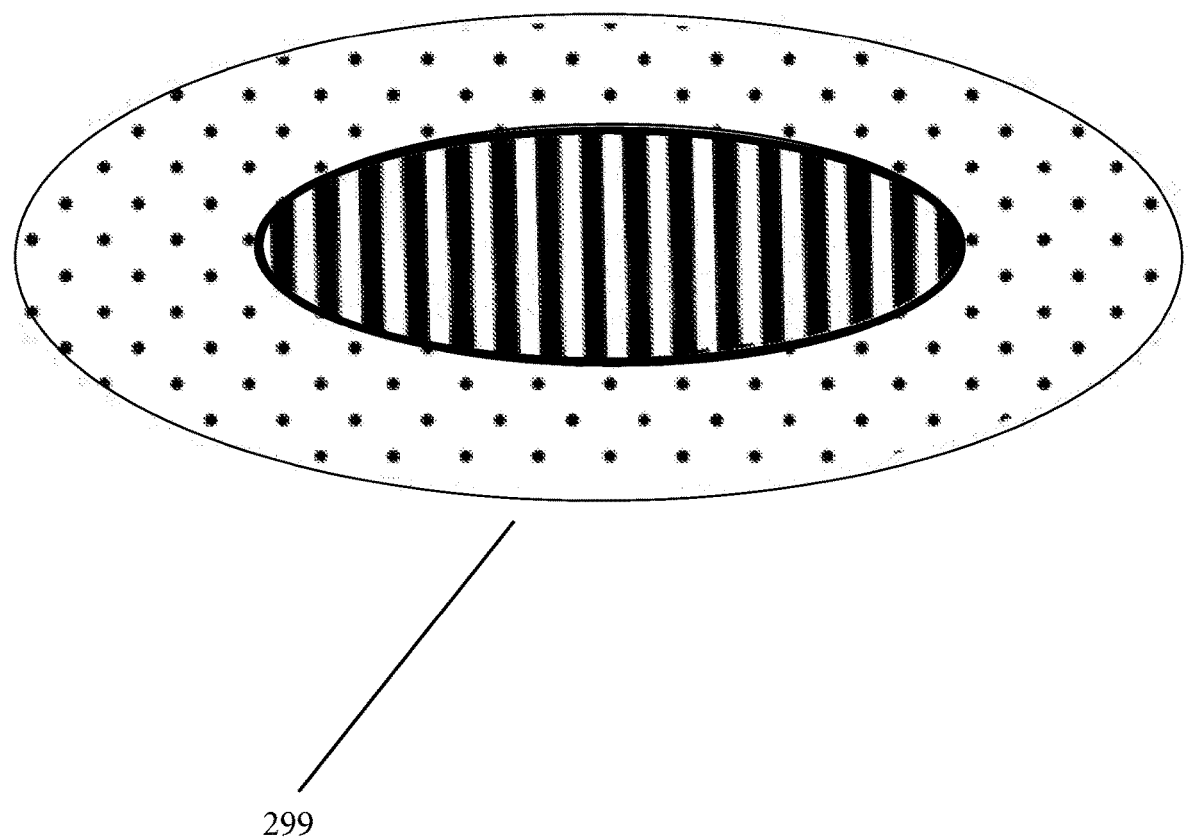
FIG. 1 is an isometric view of the complete device.

In the Summary above, this Detailed Description, the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or [[0]] as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

The all-natural material (cotton based, or a more absorbent material), will be used to form the bottom for the pad. The middle of the cotton pad will have an indentation to where the compacted coil (oval in shape) will be placed. The all-natural cotton based material will surround all areas of the compacted coil except for the top portion of the compacted coil. The top of the compacted coil is in place to ensure all bodily fluids, such as menstrual cycles, urination (bladder_leakage), etc., will go directly to the center of the pad onto the compacted coil. This will ensure maximum usage of the NuPad. The NuPad will be packed in an all-natural (no perfumes/dyes) material to keep with the all-natural concept.

In the following detailed description, the device according to the teachings for this application in the form of an improved sanitary pad containing an inner cylinder core 299 will be described. It should be noted that although a sanitary pad 299 design is described the teachings of this application can also be used in other products such as daily undergarments, incontinence products, medical products for fluid control such as surgical devices or other uses as would be known to those with skill in the art.

Figure 2:
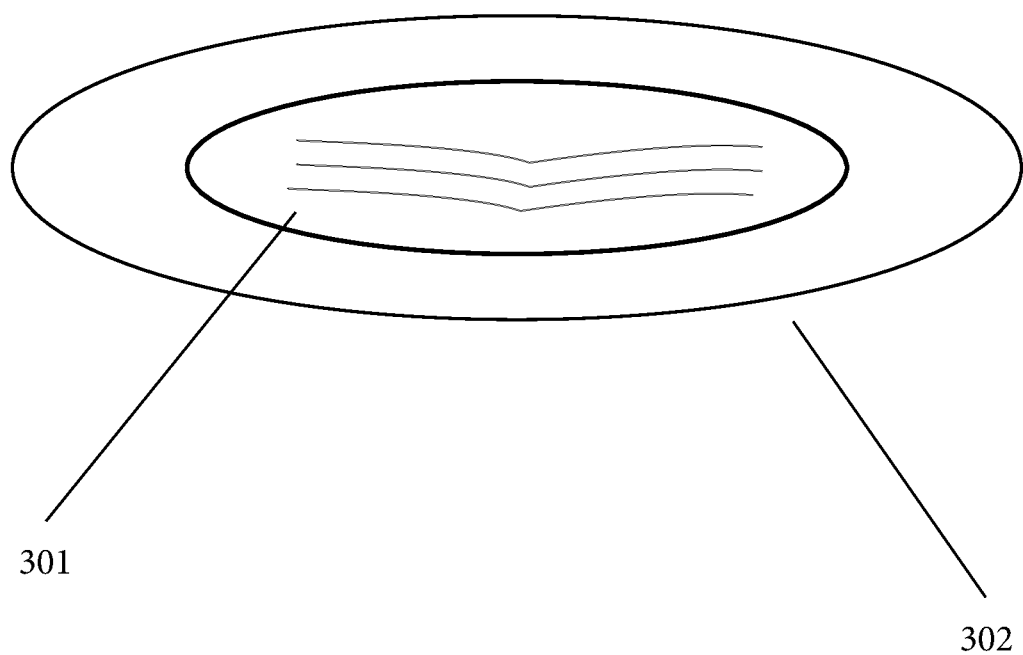
FIG. 2 is an isometric view of the device without the central core.

FIG. 1 illustrates the improved sanitary pad 299 in its entirety. FIG. 2 illustrates the indentation for the cylindrical core 301 in sanitary pad 299.

Figure 3:
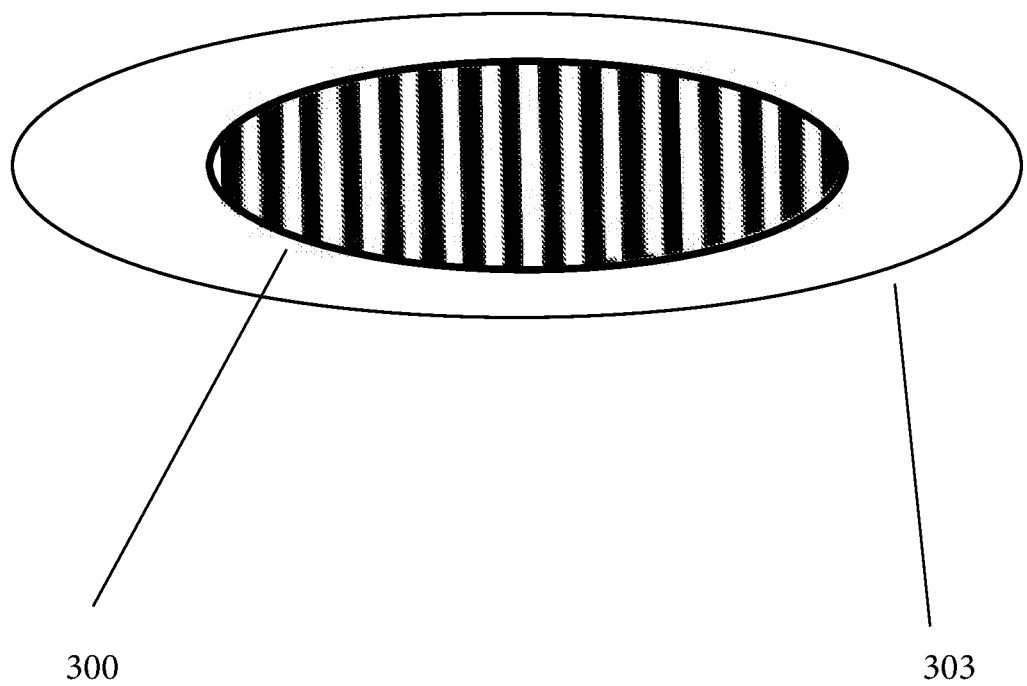
FIG. 3 is an isometric view of the device without the protective layer and the central core.

The inner cylinder core 300 is illustrated in FIG. 3. Preferably cylinder core 300's entire top layer is two ply and rippled. The outer oval segment 303 encases cylinder core 300. Preferably the cylindrical core consists of hypoallergenic all natural cotton without dyes or perfumes.

Figure 4:
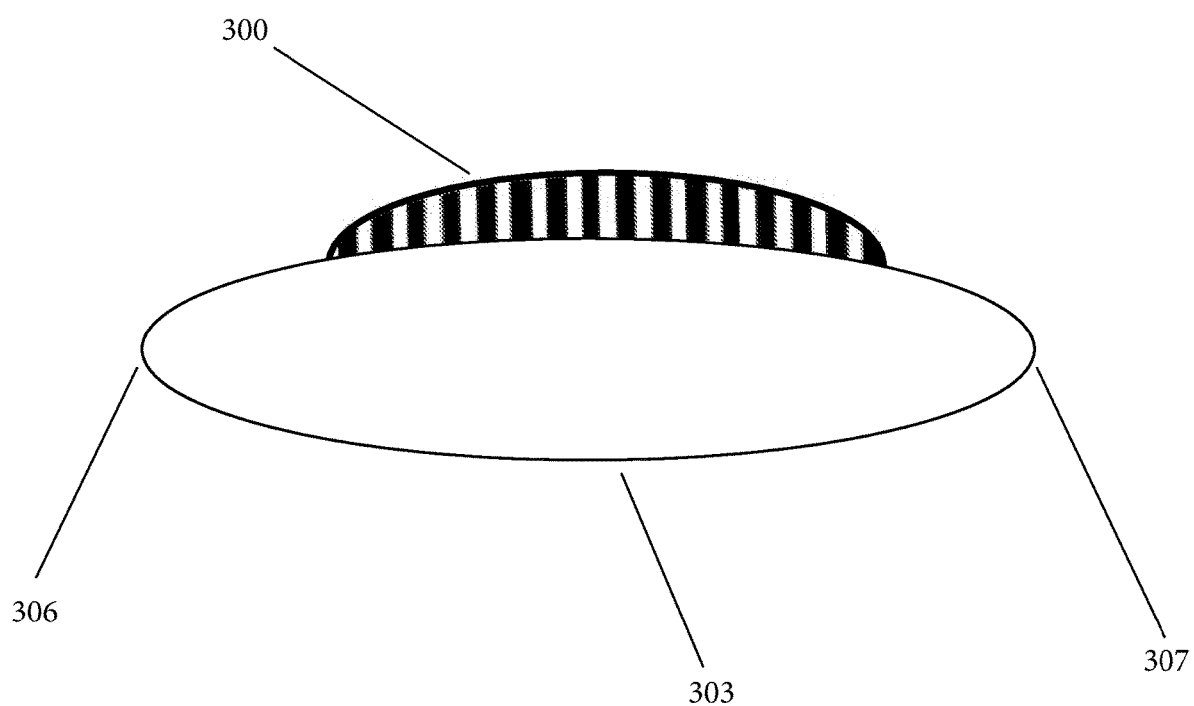
FIG. 4 is an alternative isometric side view of the device with the central core.

FIG. 4, displays a side view of sanitary pad 299. The cylinder core 300 is shown from a side angle to illustrate that cylinder core 300 protrudes outside of menstrual pad 299. The oval shape of left 306 and right 307 tip give the entire pad an oval shape. As in FIG. 3, 303 represents the entirety of the oval circumference shown here without the protective layer.

Figure 5:
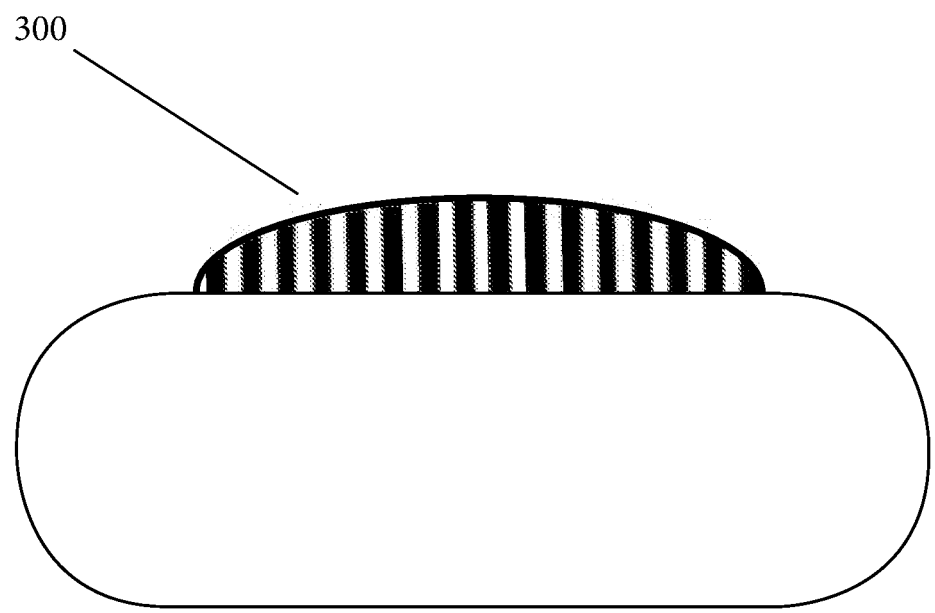
FIG. 5 is an alternative isometric side view of the device with the central core.
Figure 6:
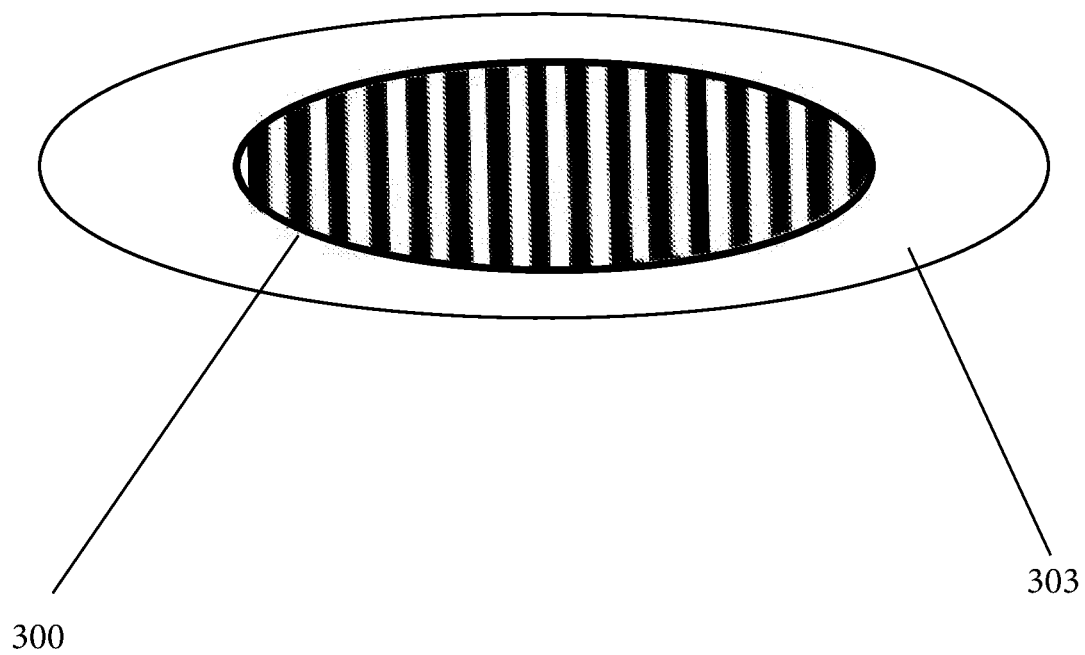
FIG. 6 is an isometric view of the device with the central core but without the protective layer.

FIG. 5 displays the menstrual pad 299 with either the left 306 or right 307 tip facing the viewer. It also displays the cylinder core 300 protruding out of the pad. Cylinder core 300 is displayed in FIG. 6 positioned centrally in sanitary pad 299. Preferably cylindrical core 300 is positioned horizontally in the pad such that the cylindrical core is surrounded by the same amount of pad on all sides in a series of horizontal planes parallel to the surface of the pad. Sanitary pad 299 is also displayed in the illustration without protective layer 310.

Figure 7:
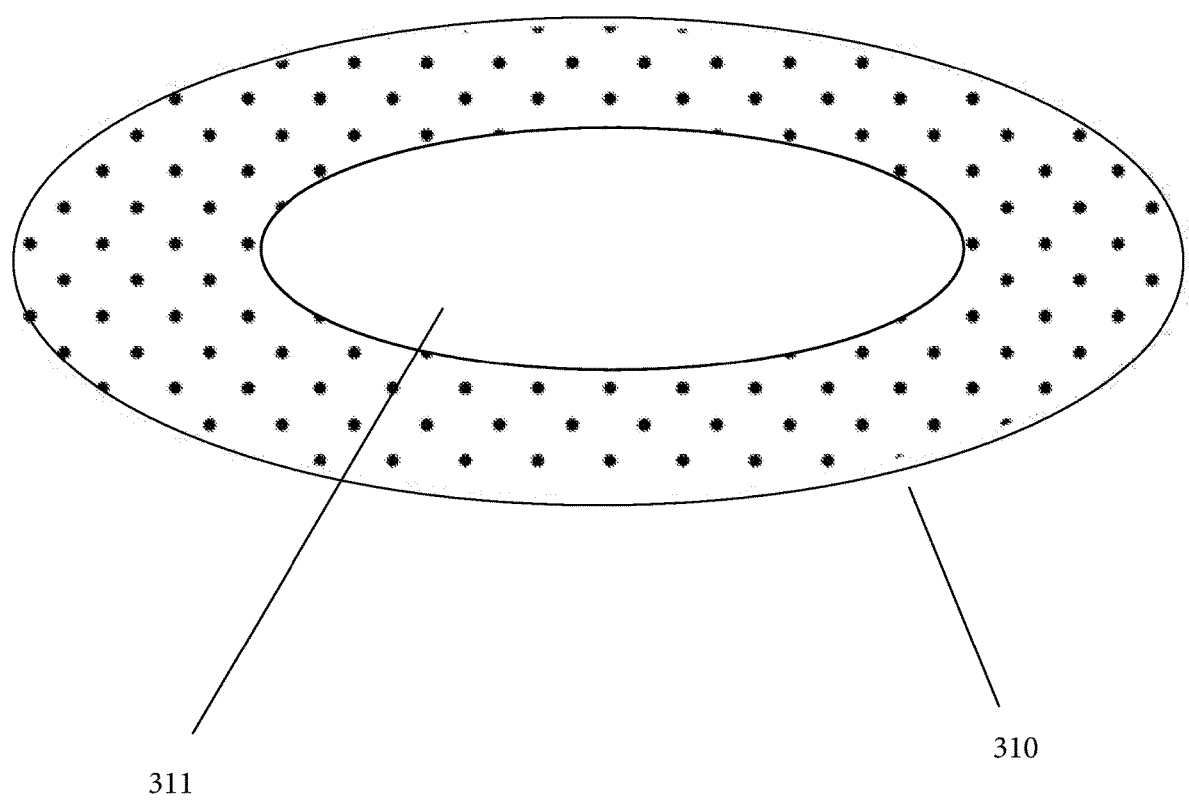
FIG. 7 is an isometric view of the protective layer associated with the device.

Protective layer 310 is illustrated in FIG. 7. Protective layer 310 preferably consists of an all-natural dry weave material. As would be obvious to those with normal skill in the art, however, other structures are possible. Cut out or opening 311 facilitates the proper placement of the protective layer around cylinder core 300. Preferably the protective layer only covers oval segment 303 but as would be obvious to those with ordinary skill in the art a protective cover for cylinder 300 is certainly possible. The circumference of cut out 311 matches the circumference of cylinder core 300.

Figure 8:
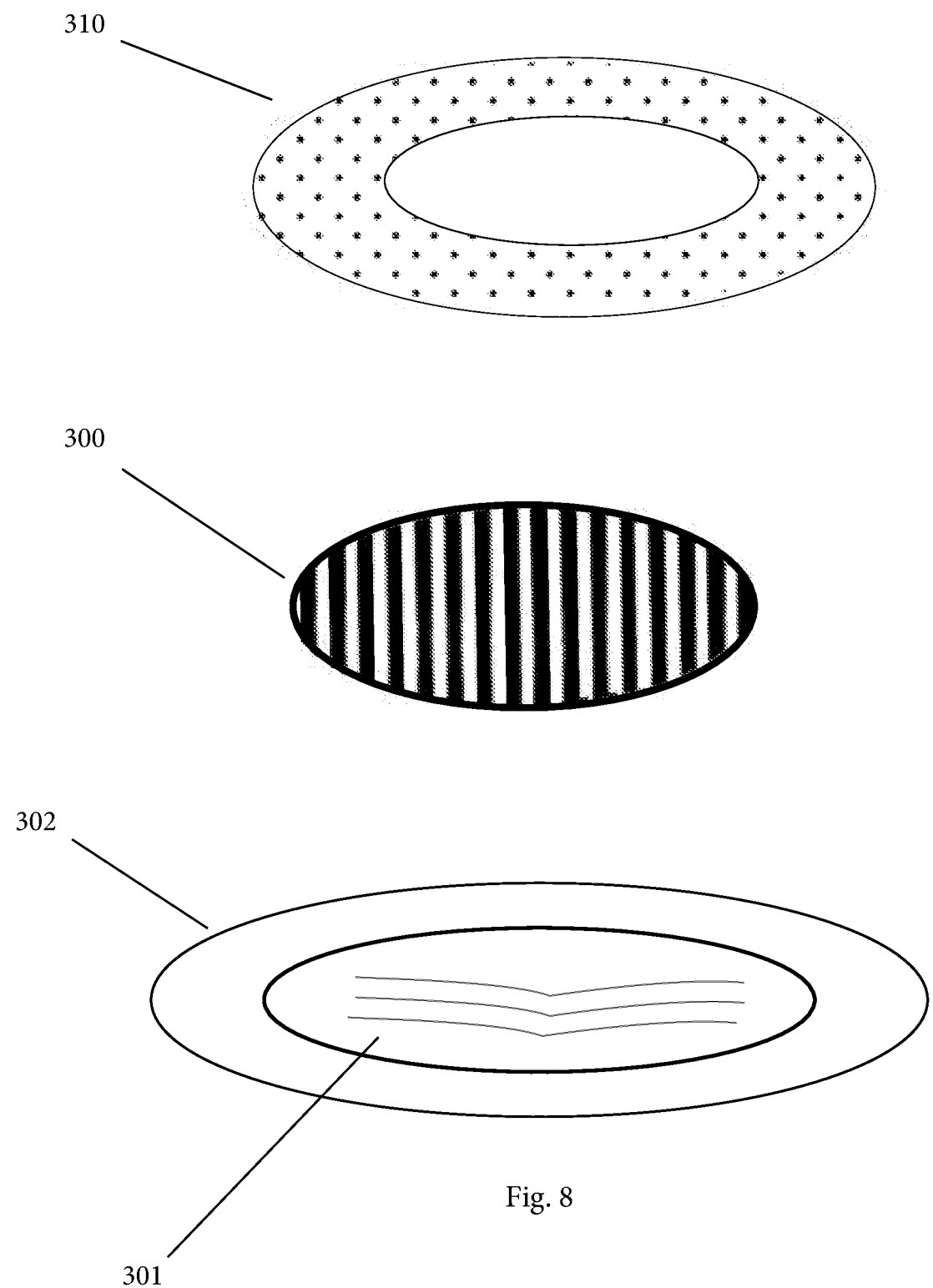
FIG. 8 is an exploded view of the layers associated with the device.
Figure 9:
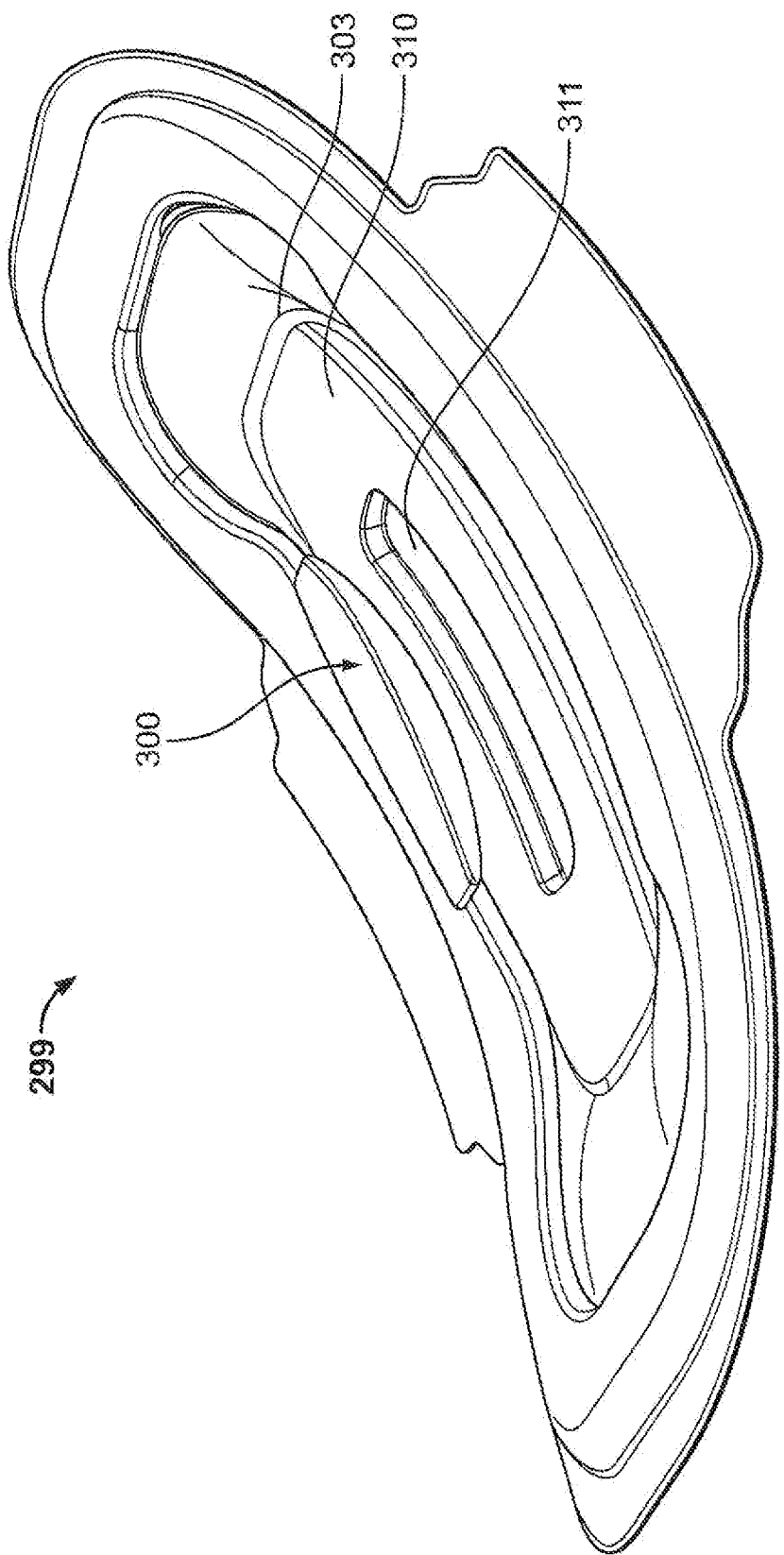
FIG. 9 is a perspective view of one of the exemplary embodiments of the device.
Figure 10:
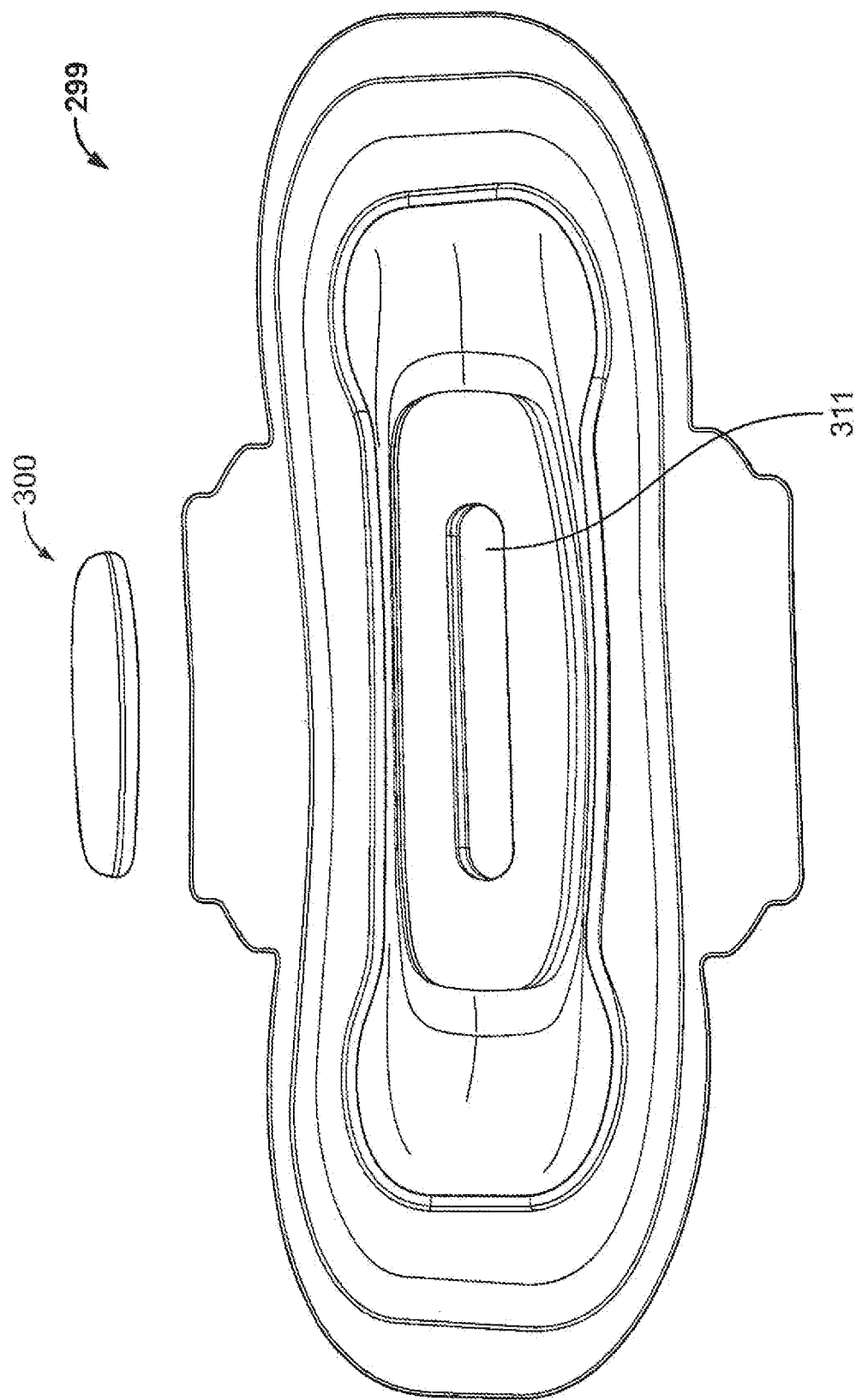
FIG. 10 is a top view of one of the exemplary embodiments of the device.
Figure 13:
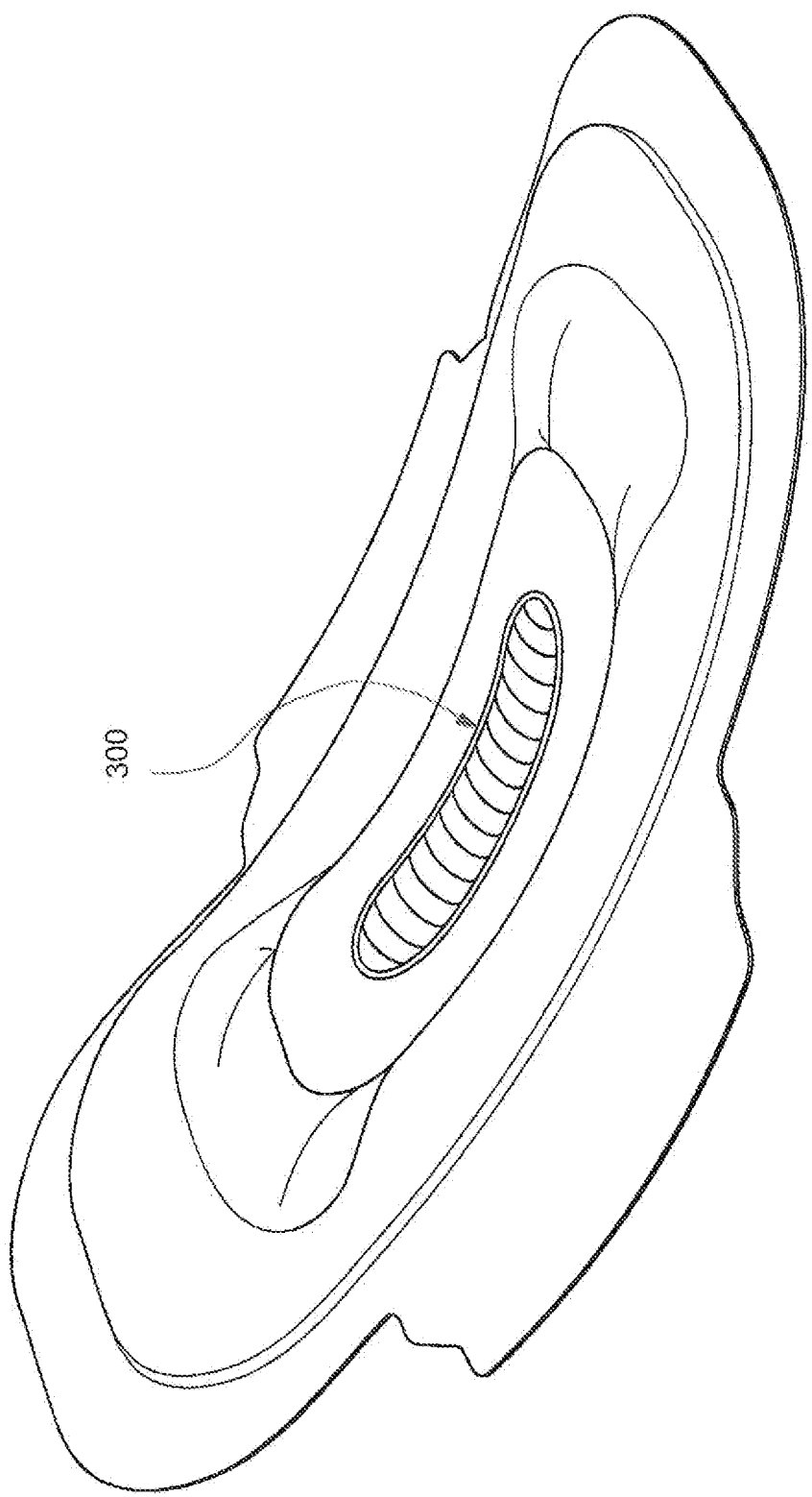
FIG. 13 is a perspective view of one of the exemplary embodiments of the device with the compacted cylindrical core.

FIG. 8 displays the layers of sanitary pad 299. The sanitary pad without the central core 302, the cylinder core 300, and the protective layer 310. Preferably each layer is produced separately and then attached to the other layers. The layers can be attached using any method known in the art including but not limited to: glue, sewing, compression, clips or any other method known to those of skill in the art.

In use the sanitary pad is preferably positioned so that the inner cylindrical core runs vertically along the outside of the vagina. When used as an incontinence product the core is aligned with the vagina, the end of the penis or the anal opening. This helps to secure the pad in place and direct flow onto the inner core. Once the inner core is full liquid seeps into the surrounding pad and it is time to consider changing the pad.

The teaching of the present application has been described in detail for purpose of illustration, it understood that such detail is solely for this purpose, and variations can be made therein by those skilled in the art without departing from the scope of the teaching of this this application. For example, the oval cylinder shape of this product has been described that is suitable for the creation of the sanitary pad, but it is understood that the shape does not need to be cylinder, the core shape can be made to be suitable for other preventive bodily fluid products, such as daily undergarments for men and women, surgeries, post hysterectomies, etc. Features described in the preceding description may be used in combinations other that the combinations explicitly described.

Whilst endeavoring in the foregoing specification to draw attention to those features of the invention believed to be of importance it should be understood that the Application claims protection in respect of any patentable feature or combination of features hereinbefore referred to and/or shown in the drawings whether particular emphasis has been paced thereon.

The term "compromising" as used in the claims des not exclude other elements or steps. The term "a" or "an" as used in the claims does not exclude a plurality. A unit or other means may fulfill the functions of several units or means recited in the claims.

Certain terminology and derivations thereof may be used in the preceding description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

What is claimed is:
1. A fluid absorbent device comprising:
a first layer comprising a cotton based or a more absorbent material, having a top surface, a bottom surface, and a substantially ovular outer edge defined by a first circumference, wherein the first layer comprises a first indentation located in the middle of the cotton based first layer in the top surface, said first indentation having a shape defined by a second circumference, and wherein the first circumference is greater than the second circumference;

a replaceable core, wherein the core has substantially the same shape and circumference as the first indentation, wherein the core can be positioned within the first indentation; and a second layer having a top surface, a bottom surface, and a substantially ovular outer edge, wherein the outer edge of the second layer has substantially the same shape and circumference as the first layer, the second layer further comprising a second opening having substantially the same shape and circumference as the core, wherein upon placement of the bottom surface of the second layer over the top surface of the first layer, the core protrudes through the second opening;

wherein the core is a compacted coil; and wherein at least thirty percent of the core protrudes above the top surface of the second layer.

2. The fluid absorbent device of claim 1, wherein the second opening facilitates proper placement of the second layer over the first layer.

3. The fluid absorbent device of claim 1, wherein the core is substantially cylindrical.

4. The fluid absorbent device of claim 1, wherein the second layer comprises an all-natural dry weave material.

5. The fluid absorbent device of claim 1, wherein the core comprises a top layer that is two ply and rippled.

6. The fluid absorbent device of claim 1, wherein the first layer comprises a dry weave hypoallergenic cotton material.

7. The fluid absorbent device of claim 1 wherein the first layer and the core comprise a dry weave hypoallergenic cotton material.

8. The fluid absorbent device of claim 1, wherein the bottom surface of the second layer is attached to the top surface of the first layer using at least one of glue, sewing, compression, or clips.

9. A fluid absorbent device consisting of:

a first layer comprising a cotton based or a more absorbent material, having a top surface, a bottom surface, and a substantially ovular outer edge defined by a first circumference, wherein the first layer comprises a first indentation located in the middle of the cotton based first layer in the top surface, said first indentation having a shape defined by a second circumference, and wherein the first circumference is greater than the second circumference;

a replaceable core, wherein the core has substantially the same shape and circumference as the first indentation, wherein the core can be positioned within the first indentation; and a second layer having a top surface, a bottom surface, and a substantially ovular outer edge, wherein the outer edge of the second layer has substantially the same shape and circumference as the first layer, the second layer further comprising a second opening having substantially the same shape and circumference as the core, wherein upon placement of the bottom surface of the second layer over the top surface of the first layer, the core protrudes through the second opening;

wherein the core is a compacted coil;

wherein the second layer comprises an all-natural dry weave material; and wherein at least thirty percent of the core protrudes above the top surface of the second layer.

* * * * *